United States Patent
Crowther et al.

(10) Patent No.: US 9,354,242 B2
(45) Date of Patent: May 31, 2016

(54) GLASS BEAD FLOW RATES TO FACILITATE IMMUNODIAGNOSTIC TEST ELEMENT MANUFACTURE

(71) Applicant: Ortho-Clinical Diagnostics, Inc., Rochester, NY (US)

(72) Inventors: Johnathan Burr Crowther, Stanton, NJ (US); Amy Louise Surowitz, Three Bridges, NJ (US); Anna Krystyna Luczak, Parlin, NJ (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 746 days.

(21) Appl. No.: 13/653,069

(22) Filed: Oct. 16, 2012

(65) Prior Publication Data

US 2014/0106466 A1    Apr. 17, 2014

(51) Int. Cl.
*G01N 33/80* (2006.01)
*G01N 33/53* (2006.01)
*G01N 21/82* (2006.01)

(52) U.S. Cl.
CPC ............ *G01N 33/80* (2013.01); *G01N 33/5304* (2013.01); *G01N 2021/825* (2013.01); *Y10T 29/49982* (2015.01); *Y10T 436/25* (2015.01)

(58) Field of Classification Search
CPC .................. G01N 33/80; G01N 2021/825
USPC ......................................................... 436/174
See application file for complete search history.

(56) References Cited

U.S. PATENT DOCUMENTS

| | | | | |
|---|---|---|---|---|
| 3,492,396 | A * | 1/1970 | Dalton | G01N 33/4905 210/198.2 |
| 4,139,604 | A * | 2/1979 | Gutcho | G01N 33/538 436/539 |
| 5,552,064 | A * | 9/1996 | Chachowski | B01L 3/5021 210/518 |

OTHER PUBLICATIONS

K.J. Reis, R. Chachowski, A. Cupido, D. Davies, J. Jakway, and T.M. Setcavage "Column agglutination technology: the antiglobulin test" Transfusion 1993;vol. 33, No. 8, pp. 639-643.*
Calibrated Microspheres Oct. 12, 2011 https://web.archive.org./web/20111012021036/http://2spi.com/catalog/standards/microspheres.shtml.*
Dextran Chemistry accessed from http://www.dextran.net/about-dextran/dextran-chemistry/physical-properties.aspx on Sep. 15, 2015.*

* cited by examiner

*Primary Examiner* — Christopher A Hixson
*Assistant Examiner* — Emily Berkeley
(74) *Attorney, Agent, or Firm* — Barclay Damon, LLP

(57) ABSTRACT

A method of preparing a glass bead mixture using inert nanoparticles to improve flow rates of the glass beads for purposes of manufacturing an immunodiagnostic test element, such as a column agglutination test cassette, and a test element made in accordance with the method.

9 Claims, 3 Drawing Sheets

GLASS BEAD FLOW RATES TO FACILITATE IMMUNODIAGNOSTIC TEST ELEMENT MANUFACTURE

TECHNICAL FIELD

The subject matter disclosed herein generally relates to the manufacture of glass beads as used in an immunodiagnostic test element and more specifically to a method for improving flow properties of the glass beads for use in a test element without interfering with the functionality thereof.

BACKGROUND OF THE INVENTION

Column agglutination technology (CAT) employs an immunodiagnostic test element, such as a cassette or card, that includes or supports a plurality of columns or chambers. A quantity of beads which are typically made from glass or similar material or, alternatively, a gel matrix are added to the columns of the test element along with a suitable reagent prior to the addition of a patient sample, such as whole blood, plasma, serum, or red blood cells. An agglutination reaction can then be created in each test chamber followed by centrifugation or agitation of the test element, thereby enabling blood typing or other tests. During centrifugation, large agglutinants are trapped above the beads while smaller agglutinants are trapped along the length of the column, within the beads or gel matrix, and smaller red blood cells (RBCs) pass therethrough toward the bottom of the column. Examples of test cassettes employing CAT are described in U.S. Pat. Nos. 5,338,689 and 5,863,802, each herein incorporated by reference in their entirety.

Efficient manufacturing of column agglutination test elements requires that the glass beads used therein be able to flow freely during a manufacturing fill step when the glass beads are initially dispensed into each of the test columns. Following their manufacture, and as received from suppliers, the glass beads typically have adequate flow rates. However, the beads also include various impurities, such as dust, oils and soda ash, which would prevent overall consistency in use. Therefore, the beads are washed prior to filling the columns of a test element. Though the washing operation removes the impurities, this process also produces attractive forces between the beads that can significantly retard the flow rates of the beads and impact manufacturing time in filling the chambers of a test element.

Type I borosilicate glass beads of approximately 50-120 μm diameter are typically used in the manufacture of column agglutination test elements. The clean smooth surface of the beads causes each bead to associate, or cohere, to adjacent beads at their contact points. This cohesion force negatively impacts the ability of the beads to flow. Thus, there is a need to enhance flow rates of cleaned glass beads and to minimize the variability of flow rates among different batches of cleaned beads in order to reduce manufacturing machine downtime.

BRIEF DESCRIPTION OF THE INVENTION

Ongoing studies have shown glass bead blending with trace amounts of chemically inert nanoparticles, such as fumed silica, result in significant enhancement of the flow rate of glass beads and can improve the test element filling process. Since the cleaned and dried beads cannot flow freely due to strong attractive forces between the cleaned beads, it becomes advantageous to disrupt those forces through the addition of inert nanoparticles, such as fumed silica. These nanoparticles adhere to the exterior surface of the glass beads, causing surface imperfections which disrupt the attractive forces between the glass beads and improve their flow properties. Advantageously, the addition of fumed silica or other suitable inert nanoparticles has no impact on the function or efficacy of the test element. A small amount of added fumed silica, e.g., at the rate of about 0.0001% to about 1.0% by weight, provides significant flow improvement during manufacture. The presence of aqueous reagent in the columns effectively eliminates the association of the nanoparticles with the glass beads and therefore does not interfere with the subsequently created agglutination reaction.

One embodiment comprises the step of washing a plurality of glass beads, then placing the glass beads in a mixing apparatus together with a quantity of inert nanoparticles, and mixing them together using the mixing apparatus. The inert nanoparticles are broken down into smaller particles during the mixing step. Preferably, the glass beads and the nanoparticles are made from substantially the same material.

Another embodiment comprises a method of manufacturing an immunodiagnostic test element having a plurality of test columns. The method comprises washing a plurality of glass beads. The beads are then placed in a mixing apparatus together with a preselected quantity of inert nanoparticles and are mixed or blended. The inert nanoparticles are broken down into smaller particles during the mixing. An aqueous reagent and the glass bead/nanoparticle mixture are placed in the test columns, either one at a time, in any sequence, or simultaneously. This admixture eliminates the adhesion of the inert nanoparticles to the glass beads. The glass beads and the nanoparticles are preferably made from substantially the same material.

According to another aspect, an immunodiagnostic test element comprises a planar substrate that supports a plurality of test columns formed in a linear array and in which each test column includes an aqueous reagent, glass beads and a preselected quantity of inert nanoparticles.

These, and other, aspects and objects of the present invention will be better appreciated and understood when considered in conjunction with the following description and the accompanying drawings. It should be understood, however, that the following description, while indicating preferred embodiments of the present invention and numerous specific details thereof, is given by way of illustration and not of limitation. For example, the summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The figures below are intended to be drawn neither to any precise scale with respect to relative size, angular relationship, or relative position nor to any combinational relationship with respect to interchangeability, substitution, or representation of an actual implementation.

BRIEF DESCRIPTION OF THE DRAWINGS

FIG. 4 is a comparative table of flow rates of the glass beads based upon preparation.

DETAILED DESCRIPTION

Throughout the following discussion, several terms such as "outer", "inner", "top", "bottom", "above" and "below" are used in order to provide a suitable frame of reference with regard to the accompanying drawings.

The term "sample" means a volume of a liquid, solution or suspension, intended to be subjected to qualitative or quantitative determination of any of its properties, such as the presence or absence of a component, the concentration of a component, etc. The embodiments of the present invention are applicable to human and animal samples of whole blood. Typical samples in the context of the present invention as described herein include blood, plasma, red blood cells, serum and suspension thereof.

The term "about" as used in connection with a numerical value throughout the description and claims denotes an interval of accuracy, familiar and acceptable to a person skilled in the art. The interval governing this term is preferably ±10%. Unless specified, the terms described above are not intended to narrow the scope of the invention as described herein and according to the claims.

Figure 1:
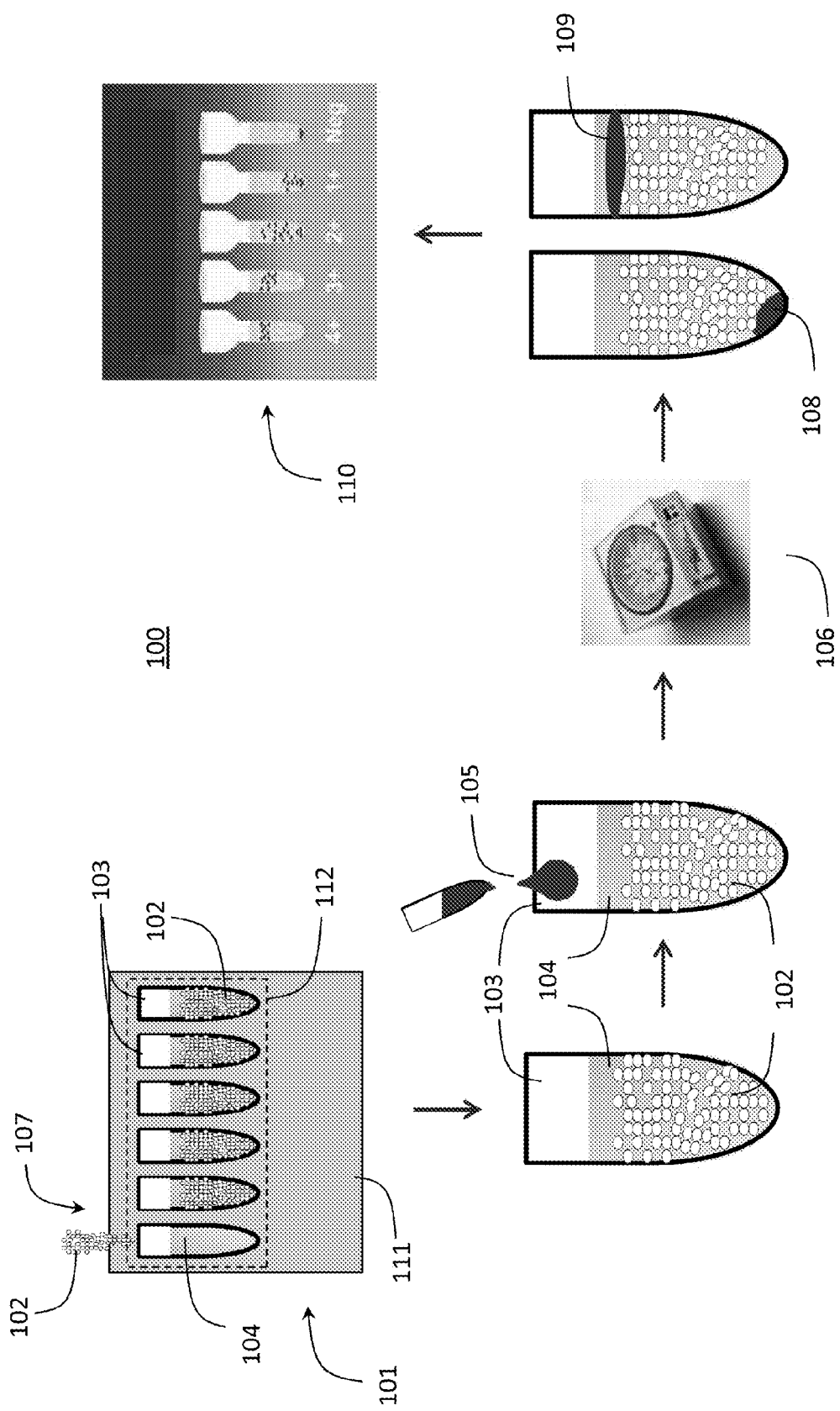
FIG. 1 is a diagram of the manufacture and use of a column agglutination test element.

Referring to the drawings, FIG. 1 illustrates an exemplary embodiment 100 of an application of micro sized glass beads having nanoparticles added thereto. More specifically, an immunodiagnostic test element 101 that employs column agglutination technology (CAT) comprises a planar substrate 111 made from a suitably rigid material, such as a plastic or other inert materials that supports a plurality of test columns 103 formed in a tubular configuration and disposed in a linear array 112. According to the present embodiment, six (6) test columns 103 are provided in parallel and are equally spaced from one another. It will be realized that the number of test columns can easily be varied. Each of the test columns 103 are sized to retain a quantity of glass beads and at least one aqueous reagent 104 for purposes of testing a patient sample, such as whole blood 105 and/or plasma, serum or red cell suspension.

When testing a blood sample 105, a quantity of a patient's blood sample 105 is dispensed in each of the test columns 103 through an opening in the top of the columns 103. The test element 101 is then centrifuged or vertically agitated to produce mixing of the sample and agglutination reagent. While being spun by the centrifuge 106, the blood descends to varying levels, based upon the size of the formed agglutinants, through the glass beads 102 and the aqueous reagent 104, as driven by the applied g forces. Depending on agglutination of the blood sample 105 in the aqueous reagent 104, all or portions of the blood sample may not pass through the glass beads 102. Agglutinated cells 109 do not pass entirely through the glass beads, while non-agglutinated red blood cells 108 continue to pass between the beads 102 and eventually sink to the bottom of the test column 103. Depending on the amount of agglutination, agglutinants may become trapped in the glass beads 102 at various levels. The characteristic agglutination pattern of the blood sample determines the reaction result of the sample 105 using a conventional agglutination pattern metric 110 for comparison. In this manner, the glass beads 102 act as a filter to the passage of blood therethrough based on agglutination properties of the blood sample and facilitate inspection so as to determine the extent of the reaction, either visually or by instrument vision.

Figure 2:
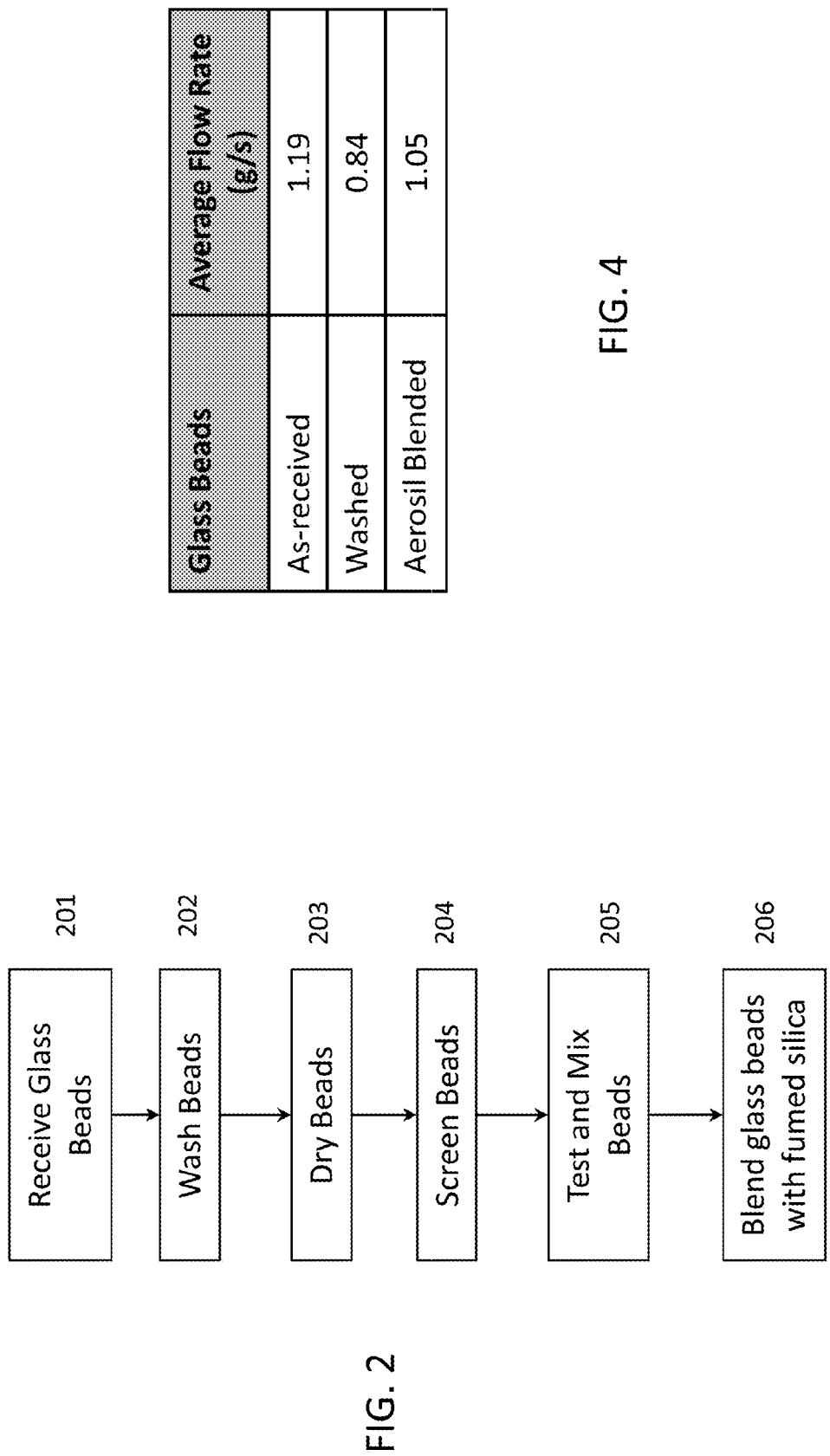
FIG. 2 is a flow diagram of a method of preparing glass beads for the manufacture of the column agglutination test element.

As noted above and in order to achieve efficient filling of the test columns 103 of the herein described test element 101 with glass beads, it is desirable to maintain uniform flow properties of the glass beads 102 from batch to batch manufacture. FIG. 2 illustrates a flow chart depicting one methodology of preparing the micro sized glass beads 102 for use in an immunodiagnostic test element, such as a cassette or test card that employs column agglutination technology. At step 201, the beads are received from a supplier in a substantially unmodifiable size. According to an exemplary embodiment, type 1, and preferably Type 1A, borosilicate glass beads ranging in size from about 50-120 µm in diameter, more preferably 65-90 µm in diameter, and even more preferably 75-90 µm in diameter, are supplied. The Type 1 and 1A designations are class designators assigned by the American Society for Testing and Materials (ASTM). The glass beads typically comprise 85-95% $SiO_2$ by weight and have an average size of about 80 µm diameter, with $Na_2O$, $B_2O_3$, and $Al_2O_3$ comprising other exemplary chemical components of the beads.

As an initial step, the unwashed glass beads can be tested for flow rates and other properties even though the wash process has yet to be performed. This test step can help to insure that the beads will flow at an adequate rate after the steps of washing the glass beads and adding nanoparticles to the glass beads, as will be described below. Other quality control requirements for incoming glass beads can include, for example, a minimal amount of discolored beads through visual inspection or other means, a minimum requirement for spherical conformity, as well as verification of a specified range of particle sizes, and a maximum amount of particular contaminants.

The presence of contaminants and/or impurities on the surfaces of the glass beads can cause the blood cells to adhere to the beads and impact functionality and consistency of the test element. For example, soda ash and oils may appear on the surface of glass beads as a byproduct of their manufacture. To remove these and other contaminants from the surface of the supplied glass beads, an exemplary acid wash is performed at step 202, including rinsing the glass beads in distilled water. An alternative additional wash can be performed which includes a caustic wash, before or after the acid wash, and a rinse step using distilled water. At step 203, the washed beads are dried in an oven. It should be noted that the caustic and acid washes, and the drying step, are well known and familiar to those having ordinary skill in the art. These cleaning steps are not essential to the present invention and may be replaced with equally effective cleaning and drying procedures. Such other procedures are considered to be equivalent and interchangeable substitutes for the washing and drying steps described herein and included in the claims below. At step 204, the glass beads are screened or sifted to separate any residual clumps.

At step 205, the glass beads are then tested for flow rates using a Hall Flow meter, which is a standardized calibrated steel funnel, or a similar apparatus. At this point, a minimum flow rate may be required depending on manufacturing processes, in particular, on the tools used for filling the column agglutination test element 101. To increase consistency of flow rates for beads across batches, the batches that have undergone the preparation steps described above can be categorized according to their measured flow rates. To achieve consistency in flow rates across batches, they can be mixed together. For example, two batches can be placed in an appropriately sized container and manually mixed using a spoon or the two batches can be flowed through a sieve.

At step 206, inert nanoparticles are blended with the washed glass beads to improve the flow rates of the washed glass beads. According to the present embodiment, hydrophilic fumed silica is utilized, comprising about 99% or more $SiO_2$ by weight, formed as chained agglomerates of spherical $SiO_2$ particles. Fumed silica is a common commercial product available from several manufacturers, for example, Evonik Degussa Corporation, Cabot Corporation, Wacker Chemie-Dow Corning, and others. More specifically, and in accordance with one embodiment, the AEROSIL® 380 brand of fumed silica is used as the source of nanoparticles blended with the glass beads.

Still referring to step 206, the blending of the glass beads and fumed silica can be performed according to the following embodiment, as an example. A predetermined quantity of glass beads, e.g., about 20 kg, is placed in a Patterson-Kelley V-blender. A small amount of fumed silica particles, e.g., about 0.2 g, is added to the V-blender and the V-blender is then run for about three minutes at about 24 revolutions per minute (RPM). This step allows the fumed silica nanoparticles to substantially and uniformly blend with the glass beads. The amount of added fumed silica is preferably about 0.0001% to about 1.0% by weight, more preferably about 0.0005% to about 0.1% by weight, and even more preferably about 0.0005% to about 0.0015% by weight, which provides adequate glass bead flow rates during test element manufacture.

Figure 3:
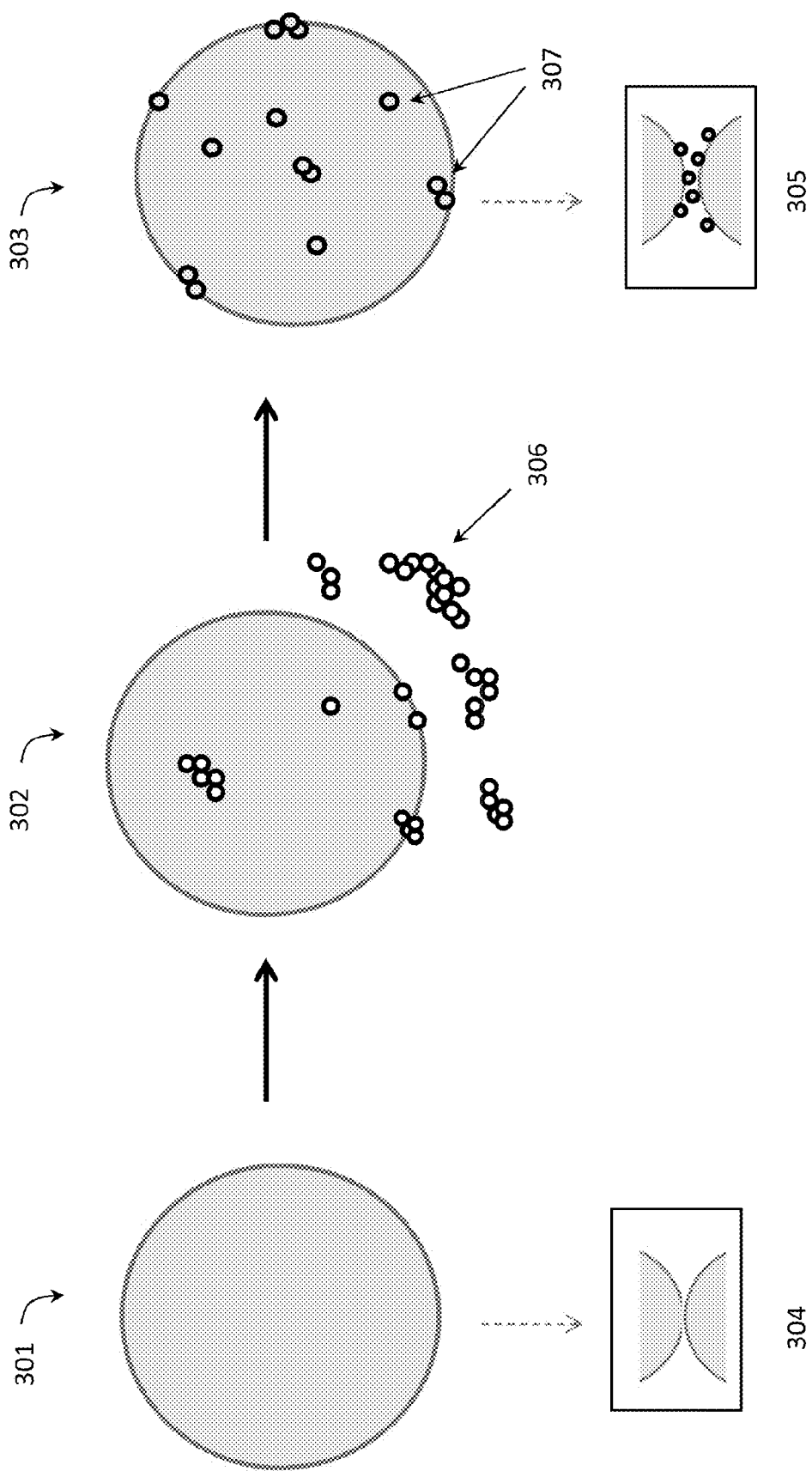
FIG. 3 depicts the effect of inert nanoparticles on the surfaces of the glass beads during blending.

FIG. 3 illustrates this blending process. During blending, the hardness of the glass beads 301 is sufficient to break apart the mechanically entangled fumed silica agglomerates 306 into smaller substantially three-dimensional aggregates 307, effectively dispersing the fumed silica between the glass beads, wherein the aggregates have a size of about 0.1 µm to about 0.2 µm. The aggregates 307 themselves are comprised of fused primary particles, wherein each of the primary particles have a size of about 7 nm in diameter, which adhere to the surface of the glass beads in aggregated form and disrupt the physical attraction between the glass beads. Considering the 7 nm primary particle and 80 µm glass bead as described above, the diameter/size ratio of the glass bead to the primary nanoparticle according to this exemplary embodiment is about 11,429.

Based on the above described blending of inert nanoparticles with the glass beads, a significant increase in flow rates is provided. Referring to FIG. 4, comparative data over a number of batches was collected wherein measured flow rates increase from an average of about 0.84 g/s (grams per second) for washed glass beads to an average of about 1.05 g/s, for washed beads that have inert nanoparticles added. It should be noted that use of a V-blender for blending dry particles is well known and familiar to those having ordinary skill in the art. The particular equipment, quantities, durations, and other blending steps described herein can be replaced with equally effective known blending techniques and so are considered to be included in the claims below.

FIG. 3 illustrates the resulting effect of the interspersed nanoparticles contributing to the improved flow rate of the washed glass beads. Initially, the surface of a washed glass bead 301 is in direct contact with the surface of a neighboring glass bead, as shown at 304. This causes the glass beads to cling to each other due to cohesion forces such as physical cohesion forces (e.g., Van der Waals, electrostatic forces), or other chemical cohesion forces caused by the close proximity of the abutting glass beads. By mixing the fumed silica agglomerates 306 with the glass beads 302, the added nanoparticles break apart into aggregates 307 and adhere to the surface of the washed glass bead 303 and, in effect, replace the attractive forces between neighboring glass beads with subsidiary adhesive forces. That is, the fumed silica nanoparticles act to separate the washed glass beads, as shown in 305, and reduce the cohesion forces between the washed glass beads 304. Thus, the nanoparticles maintain a separation between the glass beads, which results in reduced adhesion between beads and improved flow rates. The increased flowability of the glass beads aids in the column fill procedure by increasing glass bead flowability and reducing bottlenecks and down time during the column fill operation. FIG. 4 shows a table of the glass bead flow rates at three different points in the glass bead treatment process—as received, after washing, and after fumed silica blending.

Following the column fill operation when aqueous agglutination reagent and the glass beads/nanoparticles are dispensed in each of the test columns as part of the test element manufacture, the attractive forces created between the fumed silica particles and the glass beads are easily diffused and the nanoparticles separate into solution. As a result, the nanoparticles permit adequate flow rates to be maintained during the fill procedure but do not interfere with the remainder of test element manufacture or intended test protocol due to their small relative size.

PARTS LIST FOR FIGS. 1-4

100 application of glass beads with added nanoparticles
101 test element
102 glass beads
103 test columns
104 aqueous reagent
105 blood sample
106 centrifuge
107 poured glass beads
108 descended blood sample
109 undescended blood sample
110 column agglutination reactions
111 substrate
112 linear array
201 step—receive glass beads
202 step—wash glass beads
203 step—dry glass beads
204 step—screen beads
205 step—test and mix glass beads
206 step—blend glass beads with fumed silica
301 washed glass bead
302 mixing of glass beads and fumed silica
303 glass bead with adhered nanoparticles
304 glass bead surface contact
305 glass bead surfaces separated by nanoparticles
306 nanoparticle agglomerates
307 nanoparticle aggregates This written description uses examples to disclose the invention, including the best mode, and also to enable any person skilled in the art to practice the invention, including making and using any apparatus or system and performing any incorporated methods. The patentable scope of the invention is defined by the claims below, and may include other examples that are practiced by those skilled in the art. Such other examples are intended to be within the scope of the claims below if they have structural elements that do not differ from the literal language of the claims, or if they include equivalent structural elements with insubstantial differences from the literal language of the claims.

What is claimed is:
1. An immunodiagnostic test element comprising:
  a planar substrate;
  a plurality of test columns supported by said planar substrate, said plurality of test columns being disposed in a linear array in which each of said test columns contain a plurality of micro-sized glass beads and a preselected quantity of inert nanoparticles, the inert nanoparticles comprising fumed silica, wherein the fumed silica nanoparticles are adhered to an exterior surface of the micro-sized glass beads in order to disrupt attractive forces between the micro-sized glass beads and improve flow properties of the micro-sized glass beads.

2. The test element of claim 1, wherein each of said plurality of test columns further contain at least one aqueous reagent in which the aqueous reagent destroys the bonding of the inert fumed silica nanoparticles to the micro-sized glass beads.

3. The test element of claim 2, wherein each of said plurality of test columns are made of a substantially clear and substantially rigid material.

4. The test element of claim 3, wherein the micro-sized glass beads comprise borosilicate having a size between about 50-120 μm in diameter.

5. The test element of claim 3, wherein the micro-sized glass beads comprise borosilicate having a size of between about 75-90 μm in diameter.

6. The test element of claim 3, wherein the micro-sized glass beads comprise borosilicate having a size of between about 65-90 μm in diameter.

7. The test element of claim 1, wherein the preselected quantity of inert nanoparticles comprises about 0.0001% to about 1.0% of the weight of the micro-sized glass beads.

8. The test element of claim 1, wherein the preselected quantity of inert nanoparticles comprises about 0.0005% to about 0.1% of the weight of the micro-sized glass beads.

9. The test element of claim 8, wherein the preselected quantity of inert nanoparticles comprises about 0.0005% to about 0.0015% of the weight of the micro-sized glass beads.

* * * * *